United States Patent
DiMatteo et al.

(10) Patent No.: US 7,617,823 B2
(45) Date of Patent: Nov. 17, 2009

(54) BLOWER MOUNTING ASSEMBLY

(75) Inventors: Mark DiMatteo, Irwin, PA (US);
Michael E. Mort, Somerset, PA (US);
Jeffrey Kepler, Export, PA (US)

(73) Assignee: RIC Investments, LLC, Wilmington, DE (US)

( * ) Notice: Subject to any disclaimer, the term of this patent is extended or adjusted under 35 U.S.C. 154(b) by 602 days.

(21) Appl. No.: 11/210,976

(22) Filed: Aug. 24, 2005

(65) Prior Publication Data
US 2007/0048159 A1 Mar. 1, 2007

(51) Int. Cl.
A61M 16/00 (2006.01)
F01D 5/00 (2006.01)

(52) U.S. Cl. .......................... 128/204.18; 128/204.21; 415/119

(58) Field of Classification Search ............ 128/204.18, 128/200.24, 205.18, 205.25, 204.24; 181/212; 248/638, 634; 417/363, 423.15, 423.14; 415/119, 214.1
See application file for complete search history.

(56) References Cited

U.S. PATENT DOCUMENTS

| | | | | |
|---|---|---|---|---|
| 5,470,363 A | * | 11/1995 | Leader et al. .................. | 96/385 |
| 5,501,433 A | * | 3/1996 | Satori .................... | 267/140.13 |
| 6,016,838 A | * | 1/2000 | Wigmore ............... | 137/625.64 |
| 6,216,691 B1 | * | 4/2001 | Kenyon et al. ......... | 128/205.18 |
| 6,315,526 B1 | * | 11/2001 | Jones ......................... | 417/363 |
| 6,371,738 B2 | * | 4/2002 | Jones ......................... | 417/363 |
| 6,439,599 B1 | * | 8/2002 | Laue et al. .................. | 280/731 |
| 6,511,288 B1 | * | 1/2003 | Gatley, Jr. .................. | 415/206 |
| 6,837,260 B1 | * | 1/2005 | Kuehn .................... | 137/315.01 |
| 7,156,624 B2 | * | 1/2007 | Shoulders ................... | 417/312 |
| 2003/0038462 A1 | * | 2/2003 | Leibach et al. .............. | 280/731 |
| 2005/0072426 A1 | * | 4/2005 | Deane et al. ........... | 128/204.26 |
| 2005/0217672 A1 | * | 10/2005 | Bengtsson et al. ..... | 123/204.18 |
| 2005/0217673 A1 | * | 10/2005 | Daly et al. ............. | 128/204.18 |
| 2006/0231097 A1 | * | 10/2006 | Dougherty et al. ..... | 128/204.18 |

OTHER PUBLICATIONS

U.S. Appl. No. 10/790,288, filed Mar. 1, 2004, Truitt.

* cited by examiner

Primary Examiner—Justine R Yu
Assistant Examiner—Annette F Dixon
(74) Attorney, Agent, or Firm—Michael W. Haas

(57) ABSTRACT

A gas delivery system comprising an external housing, a flow generator, and a vibration damper body. The flow generator is disposed in the external housing, and has a flow generator housing with a peripheral surface and a lower surface. The vibration damper body is disposed within the external housing and is formed of one or more compliant materials that are shaped to be complementary to the peripheral surface of the flow generator housing so as to engage the peripheral surface of the flow generator housing. The vibration damper body has a lower surface attached to a bottom surface of the external housing, and also has a peripheral surface formed such that at least one air gap is created between at least a portion of the vibration damper body and the external housing.

17 Claims, 6 Drawing Sheets

BLOWER MOUNTING ASSEMBLY

BACKGROUND OF THE INVENTION

1. Field of the Invention

The present invention relates generally to mounting a flow generator within an external housing of a pressure support device.

2. Description of the Related Art

Medical devices that provide a flow of gas to an airway of a patient are used in a variety of situations. For example, ventilators replace or augment a patient's own breathing, pressure support devices deliver pressurized gas to treat breathing disorders, such as obstructive sleep apnea (OSA), and anesthesia machines deliver an anesthesia gas to the patient. For purposes of the present invention, any such device that delivers a flow of gas to the airway of the patient, invasively or non-invasively, is referred to herein as a gas delivery system.

These devices include a flow generator that generates the gas delivered to the patient mounted in the pressure support system. A typical flow generator may include a brushless electric motor driving a fan or turbine, which is often referred to in combination as a blower. For purposes of the present invention, a flow generator is any device that generates the flow of gas for delivery to the patient, that elevates a pressure of gas above the ambient pressure, or both.

During operation, vibrations caused by driving the fan or turbine, i.e., the flow generator, may cause operating noise associated with the gas delivery system in which the flow generator is mounted. Additionally, the air drawn into the gas delivery system to an inlet associated with the flow generator may also cause operating noise.

Conventional attempts to minimize the operating noise caused by the flow generator within the gas delivery system have proved ineffective, inefficient, and/or expensive. Therefore, a need exists for a mounting assembly for mounting a flow generator within a gas delivery system that effectively and efficiently reduces operating noise caused by the flow generator.

BRIEF SUMMARY OF THE INVENTION

One aspect of the invention relates to a gas delivery system comprising an external housing, a flow generator, and a vibration damper body. The flow generator is disposed in the external housing, and has a flow generator housing with a peripheral surface and a lower surface. The vibration damper body is disposed within the external housing and is formed of one or more compliant materials that are shaped to be complementary to the peripheral surface of the flow generator housing so as to engage the peripheral surface of the flow generator housing. The vibration damper body has a lower surface attached to a bottom surface of the external housing, and also has a peripheral surface formed such that at least one air gap is created between at least a portion of the vibration damper body and the external housing.

Another aspect of the invention relates to a gas delivery system comprising an external housing, a flow generator, and a vibration damper body. The flow generator is disposed in the external housing, and has a flow generator housing that forms a flow outlet. The vibration damper body is disposed within the external housing and is formed of one or more compliant materials that are shaped to provide an upper surface that is complementary to the peripheral surface of the flow generator housing so as to engage the peripheral surface of the flow generator housing. The upper surface of the vibration mounting body provides a flow outlet seating portion that seats the flow outlet on top of the vibration damper body.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

DETAILED DESCRIPTION OF THE EXEMPLARY EMBODIMENTS

Figure 1:
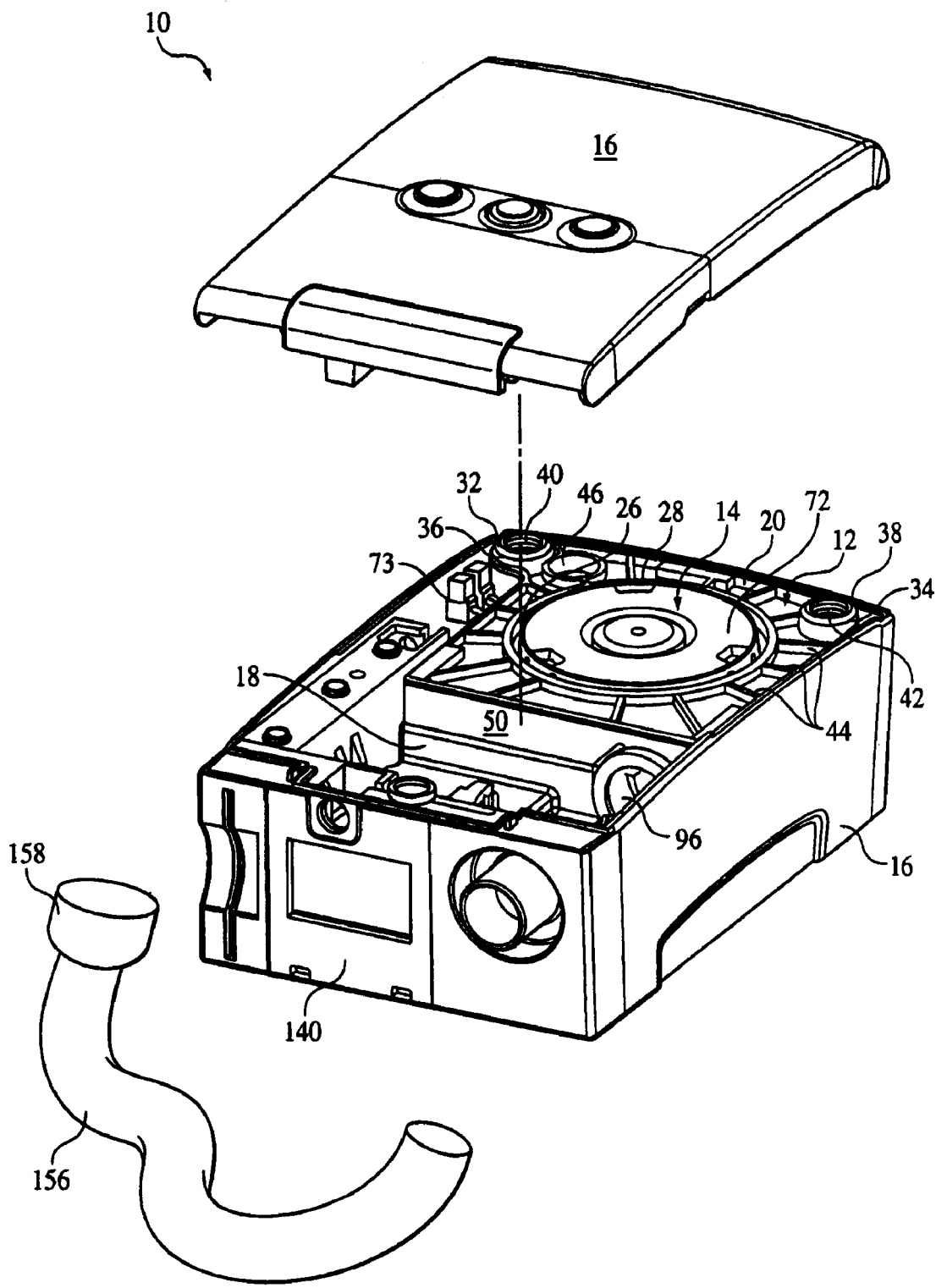
FIG. 1 is a partially exploded view of a gas delivery system including a flow generator mounting assembly, according to one embodiment of the invention.

FIG. 1 is a perspective view, partially exploded, of a gas delivery system 10 in accordance with the principles of the present invention. Specifically, the illustrated exemplary embodiment of gas delivery system 10 is used for providing a pressurized flow of breathable gas that can be delivered to a patient, such as in a continuous positive airway pressure (CPAP) device, a ventilator, a bi-level pressure support device, an auto-titrating device, and incorporates a mounting assembly 12 for mounting a flow generator in the gas delivery system in accordance with the principles of the invention.

One of ordinary skill in the art would recognize that in another embodiment of the invention, mounting assembly 12 may be implemented in any device that includes a flow generator. For example, mounting assembly 12 may be used in a display device, such as a projector or display screen, that includes a light source and/or a light modulator, such as a liquid crystal device or a micro-mirror device together with an associated flow generator or blower that must be mounted within the device, for example, for cooling or other purposes.

Figure 2:
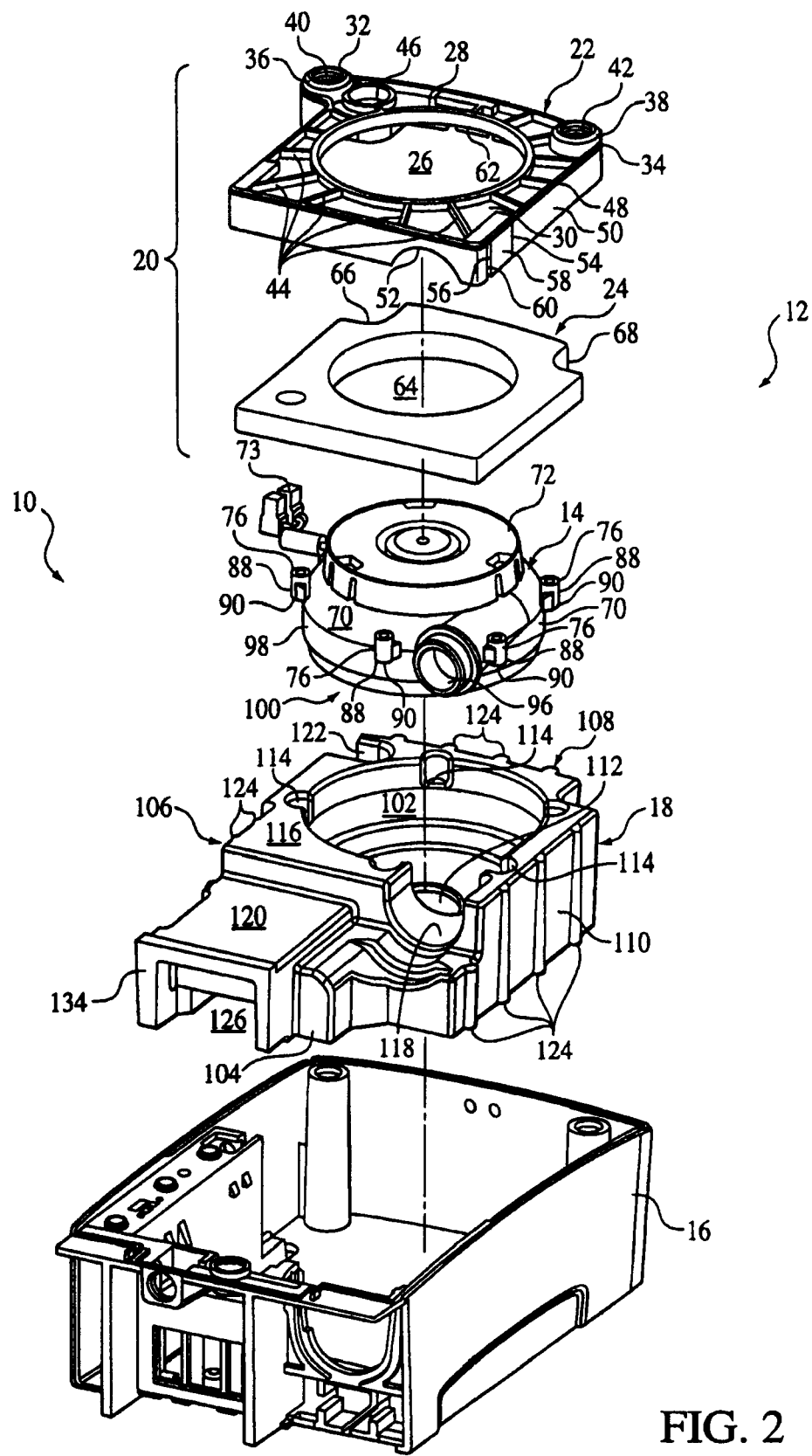
FIG. 2 is an exploded view of the gas delivery system including the flow generator mounting assembly, in accordance with one embodiment of the invention.

FIG. 2 is a partial exploded view of a gas delivery system 10 that incorporates the mounting assembly 12 for mounting a flow generator 14 within an external housing 16. In general, the mounting assembly 12 includes a main vibration damper body 18 and may also be considered to include a cover assembly 20. Cover assembly 20 includes a cover member 22 and a resilient member or vibration damper portion 24. In one embodiment, the vibration damper portion 24 is made from a foam material. It should be appreciated, however, that a rubber based or other damping material can also be used. In one embodiment, cover member 22 is formed from a substantially rigid material, such as a rigid plastic or composite material. In one embodiment, cover member 22 may be formed of a cast or stamped metal material.

A cover opening 26 is formed in cover member 22. A raised cover opening lip 28, formed on an upper surface 30 of cover member 22, defines cover opening 26. At adjacent corners of cover member 22, housing interfaces 32 and 34 are formed. In one embodiment, housing interfaces 32 and 34 include hollow protrusions 36 and 38 that protrude vertically from upper surface 30, with fastener openings 40 and 42 formed therein. A plurality of support struts 44 extend radially outward from cover opening lip 28 along upper surface 30 of cover member 22. In one embodiment, support struts 44 are formed as raised support ribs that are raised from upper surface 30 of cover member 22 such that they are flush with cover opening lip 28.

An opening 46 is formed in cover member 22 to accommodate an electronic component (e.g., a capacitor) disposed on a circuit board that is mounted over cover member 22 when gas delivery system 10 is fully assembled. Around an outer edge 48 of cover member 24, a cover member rim 50 is formed. Cover member rim 50 is provided as a substantially vertical shelf that extends from cover member 22 in both vertical directions. An arched cut-out 52 is provided in cover member rim 50 such that an arch is formed in cover member rim 50 by arched cut-out 52, with the base of the arch being formed at a bottom edge of cover member rim 50 and the apex of the arch extending upward into cover member rim 50.

A first barbed tab 54 is provided in a tab cut-out 56 formed in cover member rim 50, and extends downward from upper surface 30 of cover member 22. A barb 58 is formed on barbed tab 54 facing outward from cover member 22. By applying a force to a depressible surface 60 formed on barbed tab 54, barbed tab 54 may be elastically bent inward, with respect to cover member 22. A second barbed tab 62 and a third barbed tab (not shown) are provided on cover member 22, and are constructed similarly to barbed tab 54 and positioned within tab cut-outs formed in cover member rim 50.

As shown in FIG. 2, vibration damper portion 24 can take the form of a substantially flat member. In one embodiment, as indicated previously, vibration damper 24 may be formed from a substantially soft, pliable material. For example, an open cell foam material may be implemented. Vibration damper 24 defines an opening 64 therethrough. The size of opening 64 and the position of opening 64 on vibration damper member 24 correspond roughly to the size of cover opening 26 and the position of cover opening 26 on cover member 22. The outer footprint of vibration damper member 24 is formed to enable vibration damper member 24 to be received within cover member rim 50. Cut-outs 66 and 68 are provided in vibration damper member 24 in positions similar to a pair of ridges (not shown) that extend downwards from cover member 22, below protrusions 36 and 38.

FIG. 2 shows flow generator 14 to be mounted by mounting assembly 12.

Figure 3:
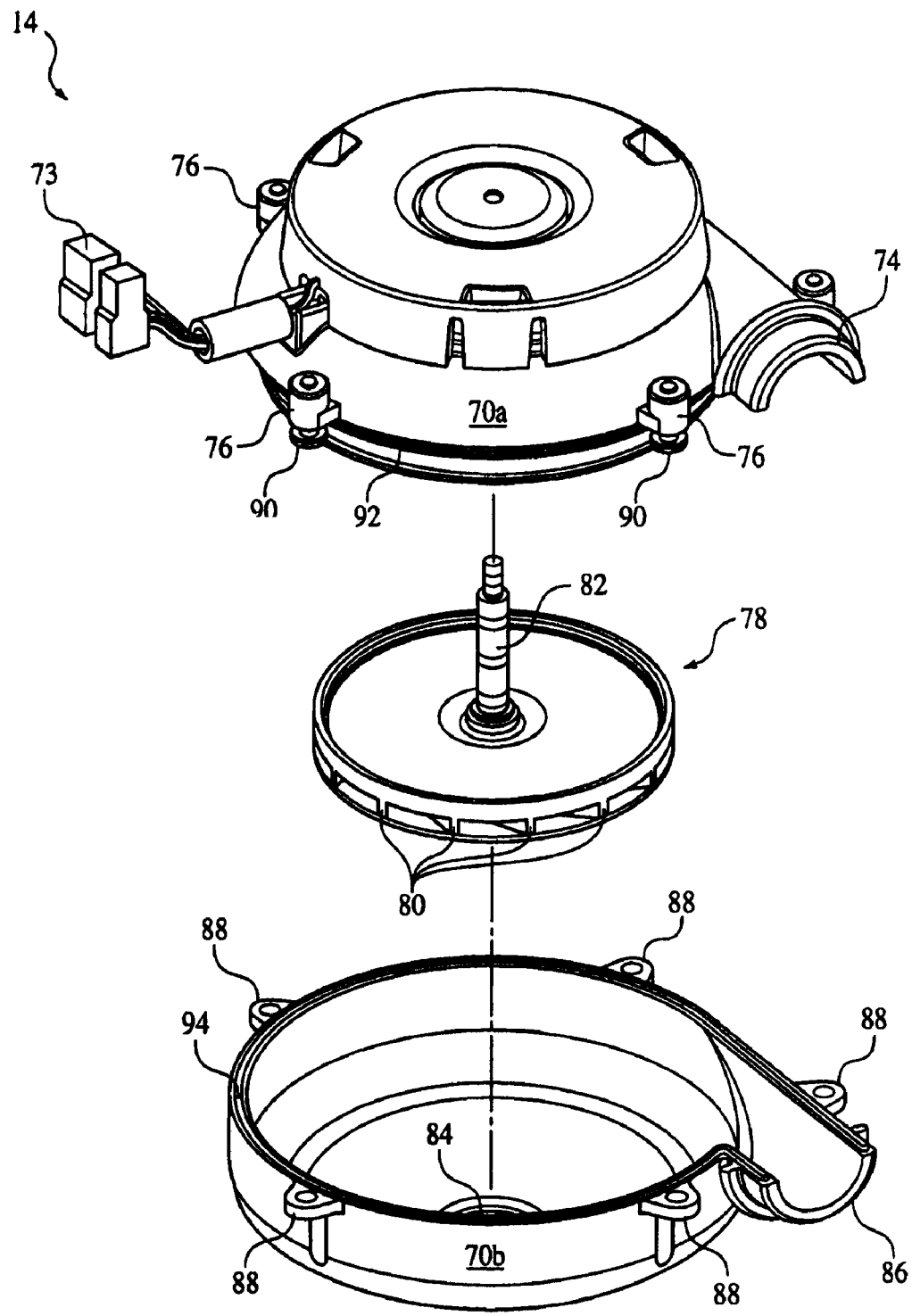
FIG. 3 is a partially exploded view of a flow generator, according to one embodiment of the invention.

In one embodiment, flow generator 14 is the flow generator 14 illustrated in FIG. 3. As can be seen in FIG. 3, flow generator 14 includes a flow generator housing 70 (illustrated as an upper housing portion 70a and a lower housing portion 70b) that encases flow generator 14. A connector 73 connects to flow generator 14 via upper housing portion 70a. An upper flow outlet portion 74 is formed by upper flow generator assembly housing 70a. A plurality of support structures 76 extend radially outward from upper housing portion 70a. A flow generator motor (not shown) is provided in upper housing portion 70a.

FIG. 3 shows a bladed rotor 78 included in flow generator 14. A plurality of blades 80 are formed on bladed rotor 78 such that when bladed rotor 78 is rotated, blades 80 force air radially outward from bladed rotor 78. A shaft 82 extends through rotational blower axis of flow generator 14. The shaft 82 is connected to the motor in upper housing portion 70a, and the motor rotatably drives the rotor 78 about the blower axis.

Lower flow generator 70b is shown in FIG. 3 as including an air inlet 84 formed at substantially the center of lower generator 70b. A lower flow outlet portion 86 is formed by lower flow generator assembly housing 70b. A plurality of support structures 88 extend radially outward from lower housing portion 70b.

As mentioned briefly above, bladed rotor 78 is inserted into upper housing portion 70a such that shaft 82 is engaged by the flow generator motor housed within upper housing portion 70a, so that the motor can rotatably drive bladed rotor 78. The motor can be controlled and/or powered via connector 73. Lower housing portion 70b is joined to upper housing portion 70a via a sealed connection, with bladed rotor 78 disposed in between, to form flow generator housing 70. Housings 70a and 70b are fastened in position with respect to each other by attaching support structures 76 to support structures 88. In one embodiment, a plurality of threaded fasteners 90 are used to attach support structures 76 to support structures 88. In other embodiments, support structures 76 and 88 may be attached via an alternative mechanism, such as a weld, an ultrasonic weld, an adhesive substance, a press-fit, a snap-fit, a friction-fit, or another mechanism.

Additionally, in one embodiment, housings 70a and 70b do not include support structures 76 and 88, and the sealed connection between housings 70a and 70b is created by attaching a rim 92 of upper housing portion 70a to a rim 94 of lower housing portion 70b. The joining of housings 70a and 70b creates a flow outlet 96 (best seen in FIG. 2) formed by upper flow outlet portion 74 and lower flow outlet portion 86. When assembled (as illustrated in FIG. 2) flow generator housing 70 includes a peripheral surface 98 disposed about the rotational blower axis, and an axially facing lower surface 100 disposed along the rotational blower axis.

When flow generator 14 operates, the bladed rotor 78 forces air contained in flow generator housing to exit housing 70 via flow outlet 96. As the air in flow generator housing 70 is forced out of flow outlet 96, air is drawn into flow generator 14 through air inlet 84.

Returning to FIG. 2, the vibration damper body 18 included in mounting assembly 12 is shown. Vibration damper body 18 is adapted for installation within external housing 16, and forms a cavity 102 shaped to receive the flow generator housing 70. Specifically, cavity 102 is shaped to be complementary to peripheral surface 98 of the flow generator housing 70 so as to engage peripheral surface 98 of flow generator housing 70. Vibration damper body 18 is formed such that an air gap is created within cavity 102 at certain regions between vibration damper body 18 and axially facing surface 100 of flow generator housing 70, as will be described in greater detail later. In addition, when vibration damper body 18 is installed within external housing 16, as will also be described below, at least one air gap is formed between external housing 16 and the peripheral surface of vibration damper body 18. In the illustrated embodiment, the peripheral surface of vibration damper body 18 includes first side 104, second side 106, third side 108, and fourth side 110.

In one embodiment of the invention, vibration damper body 18 is formed from a substantially open cell polyurethane foam having acoustic absorptive properties. It will be appreciated that although this foam is described as open cell, the terms open cell and closed cell are applicable to two extreme positions. Between the two extremes there is a continuum of variations. The flow resistivity of a foam is used to determine its degree of openness. The preferred acoustic absorptive and damping quality will be found in a foam that is located on the closed side of the middle of the range from open to closed but not at the closed cell extreme. This will provide a foam sufficiently open to absorb noise, sufficiently structurally rigid to provide the necessary mechanical support for the flow generator assembly and also sufficiently resilient to provide vibrational dampening. Additionally, although vibration damper body 18 is shown and described as being formed from a single piece of foam, in another embodiment, vibration damper body 18 is formed from a plurality of components, produced from one or more compliant materials, that are fitted adhered, or otherwise bonded to one another.

Figure 4:
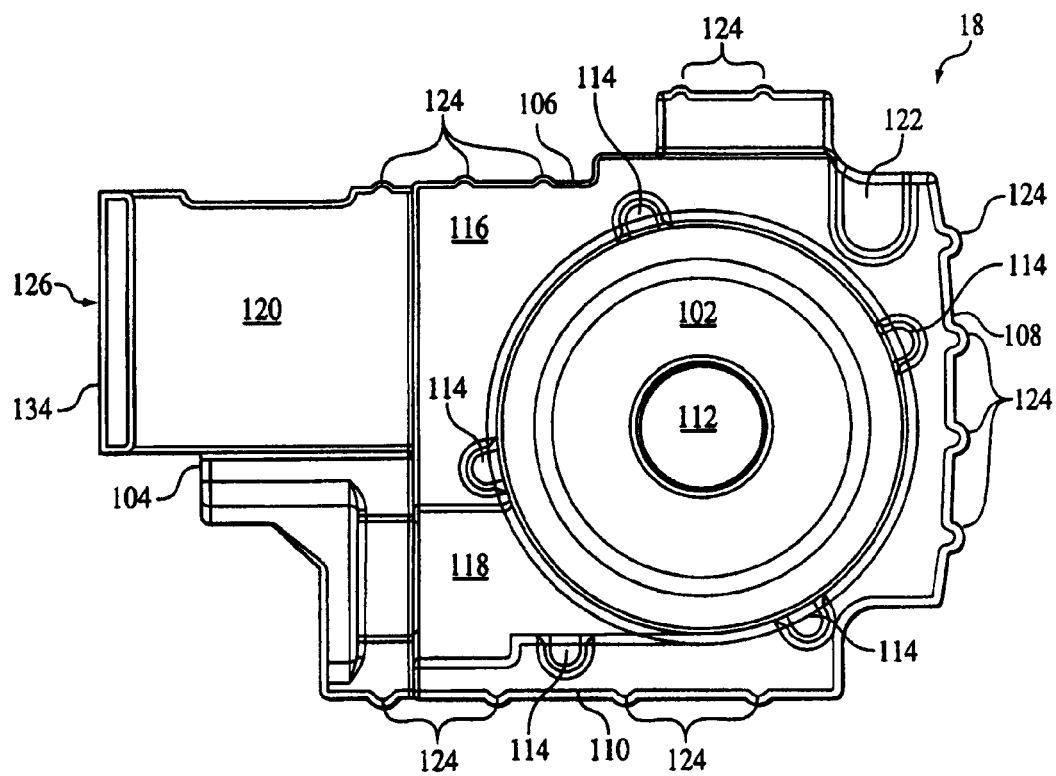
FIG. 4 is a top view of a vibration damper body, employed in the flow generator mounting assembly in accordance with one embodiment of the invention.

FIG. 4 shows a top view of vibration damper body 18, in accordance with one embodiment of the invention. Cavity 102 is formed within vibration damper body 18 to correspond roughly in size and shape with flow generator housing 70. Proximate to the center of cavity 102, a body outlet 112 is formed that communicates with cavity 102. A plurality of support surfaces 114 are formed in vibration damper body 18. In one embodiment, support surfaces 114 are formed as recesses in an upper surface 116 of vibration damper body 18 that extend radially outward from cavity 102. A flow outlet seating portion 118 of vibration damper body 18 is formed as a channel that communicates with cavity 102.

In one embodiment, vibration damper body 18 includes an electronics seating portion 120 that acts as a seat for supporting one or more electronic components (not shown) associated with the device in which vibration damper body 18 is being implemented. A cut-out 122 is formed in vibration damper body 18 to accommodate the electronic component that extends down from the circuit board (and through opening 46 of cover member 22) when gas delivery system 10 is fully assembled. On each of second side 106, third side 108, and fourth side 110 of vibration damper body 18 a plurality of body supports 124. In one embodiment, body supports 124 are formed as support ribs that are raised from sides 106, 108, and 110 of vibration damper body 18 and run substantially vertically along vibration damper body 18. On first side 104 of vibration damper body 18 a body inlet 126 is formed. Sides 104, 106, 108 and 110 are generally formed to accommodate external housing 16 and other components of the device in which vibration damper body 18 is being installed.

Figure 5:
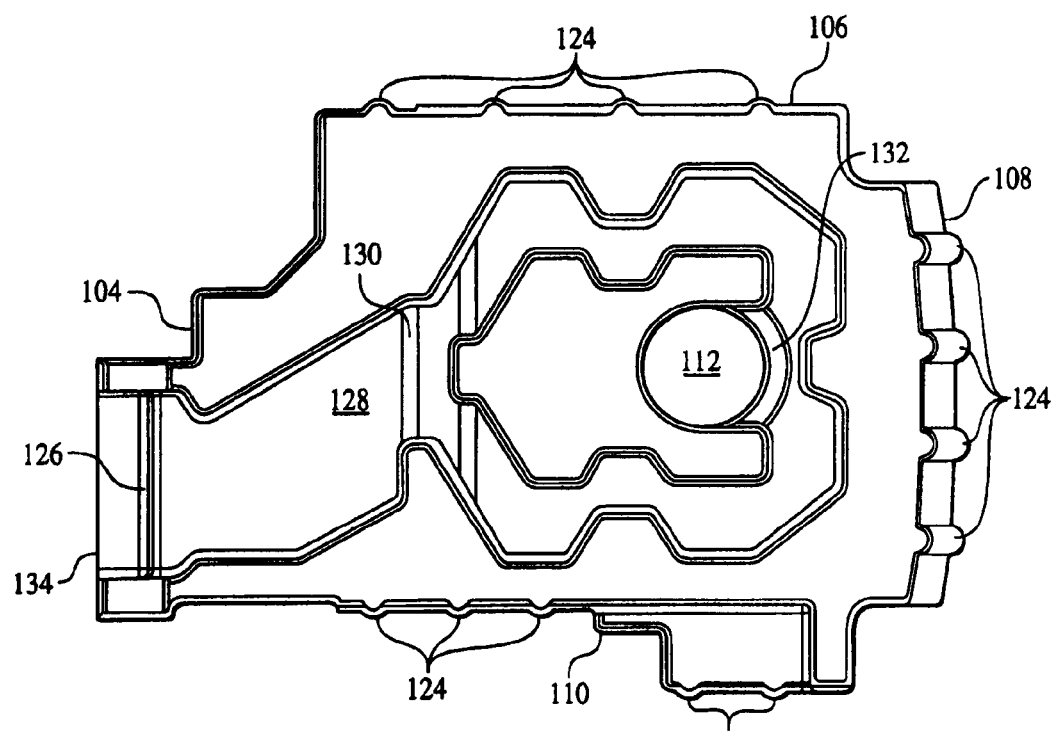
FIG. 5 is a bottom view of the vibration damper body, employed in the flow generator mounting assembly according to one embodiment of the invention.

FIG. 5 illustrates a bottom view of vibration damper body 18, according to one embodiment of the invention. As can be seen in FIG. 5, a torturous flow path 128 is formed in vibration damper body 18 from body inlet 126 to body outlet 112. Flow path 128 includes a first junction 130 at which air flowing from body inlet 126 to body outlet 112 is divided, and a second junction 132 at which air flowing from body inlet 126 to body outlet 112 is combined. At body inlet 126, an inlet body support 134 is formed as a rim around body inlet 126. It should be appreciated that other embodiments of flow path 128 exist which may or may not divide the air flowing from body inlet 126 to body outlet 112. For example, in one embodiment, flow path 128 includes a single path that wraps around body outlet 112 in the direction in which bladed rotor 78 of flow generator 14 rotates.

Figure 6:
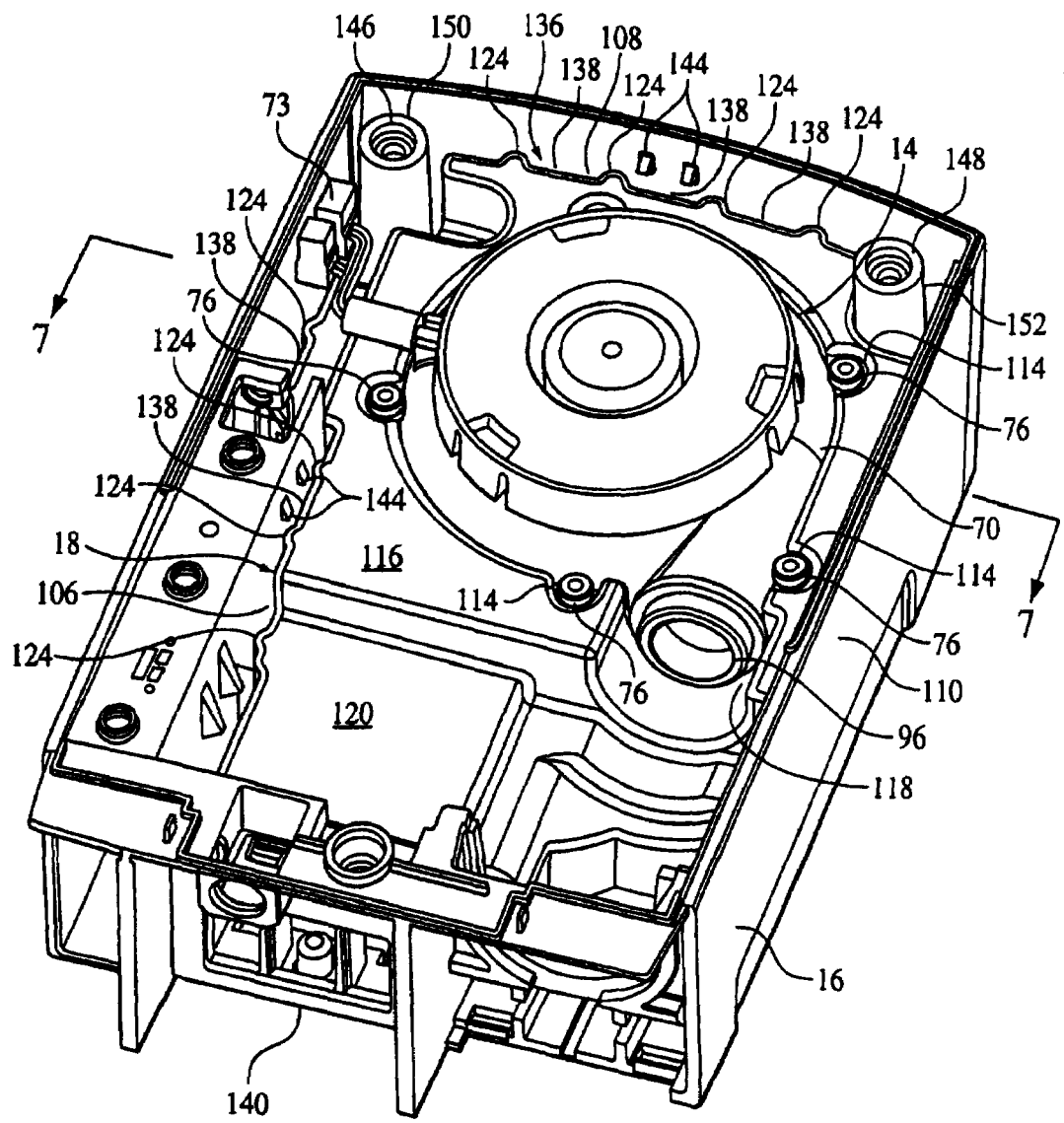
FIG. 6 is perspective view of a partially assembled gas delivery system including a vibration damper body, in accordance with one embodiment of the invention.

In FIG. 6, vibration damper body 18 is shown installed in external housing 16 and flow generator 14 is shown mounted in vibration damper body 18. As will be discussed below, when vibration damper body 18 is installed in external housing 16, body supports 124 engage with external housing 16, and support vibration damper body 18 against external housing 16 while maintaining an air gap 136 that includes a plurality of channels 138 between vibration damper body 18 and external housing 16 on second side 106, third side 108, and fourth side 110 of vibration damper body 18 formed between body supports 124. Inlet body support 134 (not visible in FIG. 6) engages external housing 16 around an inlet 140 formed in external housing 16 which allows air to pass through external housing 16 and body inlet 126 into flow path 128.

Figure 7:
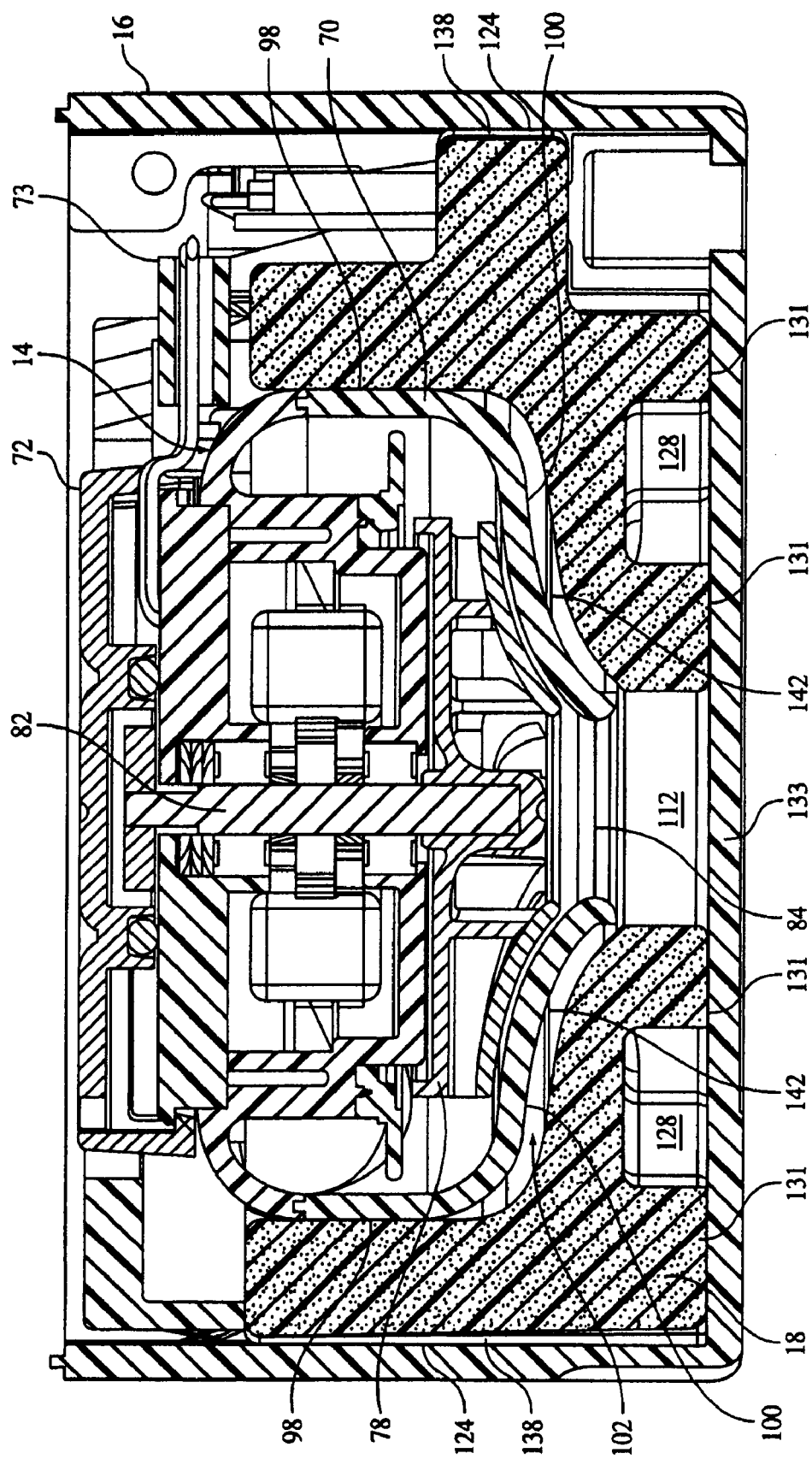
FIG. 7 is a sectional view of the partially assembled gas delivery system, according to one embodiment of the invention.

As seen in FIG. 7, when vibration damper body 18 is installed in external housing 16, a bottom surface 131 of vibration damper body 18 is attached to a floor 133 of external housing 16. In one embodiment, the bottom surface of vibration damper body 18 is attached to the floor of external housing 16 via an adhesive substance. However, in another embodiment, alterative methods for attaching the bottom surface of vibration damper body 18 to the floor of external housing 16 may be employed.

In FIG. 6, it can be seen that the shape and position of support surfaces 114 are designed to be complementary to, and engage with, support structures 76 and 88 (in the view shown in FIG. 6, structures are hidden by the recesses in vibration damper body 18 that form support surfaces 114) of flow generator housing 70 as flow generator housing 70 is introduced into cavity 102. In one embodiment of the invention, illustrated best in FIG. 2, support structures 76 and 88 are disposed on peripheral surface 98 of flow generator housing 76, radially to bladed turbine 78 encased within flow generator housing 70. Referring back to FIG. 6, flow outlet 96 is seated in flow outlet seating portion 118 of vibration damper body 18.

Turning back to FIG. 7, a sectional view of FIG. 6 is shown, taken along section lines 7-7. In the view shown in FIG. 7, an air gap 142 formed in cavity 102 between flow generator housing 70 and lower surface 100 of vibration damper body 18 is illustrated. Additionally, channels 138 that form air gap 136 between vibration damper body 18 and external housing 16 maintained by body supports 124 is also shown. When flow generator housing 70 is supported within cavity 102, air inlet 84 communicates with flow path 128 via body outlet 112.

Referring back to FIG. 1, flow generator 14 is shown fully mounted within mounting assembly 12. After flow generator 14 is disposed in cavity 102, as shown in FIGS. 6 and 7, cover assembly 20 is positioned over flow generator 14 so as to apply a force on support structures 86 and 97 and/or flow generator housing 70 that engages support structures 86 and 97 with support surfaces 114 and secures flow generator 14 within vibration damper body 18. Prior to being positioned over flow generator 14, cover assembly 20 is assembled by inserting vibration damper member 24 into cover member 22 so that vibration damper member 24 is nested in cover member rim 50 under cover member 22.

Cover opening 26 and vibration damper member opening 64 (not visible in FIG. 1) are adapted to accommodate flow generator protrusion 72 so that when cover member 22 is provided over flow generator 14 flow generator protrusion 72 is nested in cover opening 26 and vibration damper member opening 64. To secure cover assembly 20 in position, as cover assembly 20 is lowered into position over flow generator 14, barbed tab 54, second barbed tab 62, and the third barbed tab slide down along inner surfaces of external housing 16 until each of the barbs associated with the tabs clears a housing protrusion (seen best in FIG. 6, illustrated as housing protrusions 144), and becomes releasably engaged therewith. To further secure cover assembly 20 in place, housing interfaces 32 and 34 can each be secured to a corresponding cover interface (seen best in FIG. 6, illustrates as cover interfaces 146 and 148 including hollow protrusions 150 and 152) disposed within external housing 16. In one embodiment, a fastener may be provided to secured hollow protrusion 36 to hollow protrusion 150 and hollow protrusion 38 to hollow protrusion 152.

When flow generator 14 is mounted within external housing 16 by mounting assembly 12, as shown in FIG. 1, flow generator 14 may be activated.

Activating flow generator 14 causes the flow generator motor encased within flow generator housing 70 to drive bladed turbine 78 so that air is driven out of flow generator 14 via flow outlet portion 74. As was described above, as the air is driven out of flow outlet portion 74, air is drawn into flow generator 14 at air inlet 84. In one embodiment employing vibration mounting 18 as illustrated in FIG. 5, air is communicated to air inlet 84 from ambient atmosphere via body inlet 126, flow path 128, and body outlet 112. The torturous path formed by flow path 128 acts as a baffle to muffle the sound of the air rushing from body inlet 126 to body outlet 112.

The motion of the flow generator motor and/or bladed turbine 78 within flow generator housing 70 typically causes flow generator 14 to vibrate. When these vibrations are passed to members external to flow generator 14, operating noise is caused.

Securing flow generator 14 in cavity 102 by providing cover assembly 20 over flow generator 14, in the manner described above, enables an enhanced amount of the vibration generated by flow generator 14 to be dampened. Air gap 142 formed in cavity 102 between flow generator housing 70 and vibration damper body 18 diminishes the amount of vibration that is transmitted from flow generator 14 to vibration damper body 18. Air gap 136 formed between vibration damper body 18 and external housing 16 diminishes the amount of vibration that is transmitted from vibration damper body 18 to external housing 16.

It should be appreciated that although air gap 142 is described as being created by supporting a plurality of support structures 76 and 88 of flow generator 14 on support surfaces 114 of vibration damper body 18, other embodiments for creating an air gap between flow generator 14 and vibration damper body 18 within cavity exist. For example, in one embodiment the surface of vibration damper body 18 within cavity 102 includes one or more surface protrusion, such as a protruding rib, that supports flow generator 14 within cavity 102 while maintaining an air gap therebetween. Similarly, air gap 136 between vibration damper body 18 and external housing 16 may be maintained by a mechanism other than body supports 124.

In one embodiment of the invention, air gap 136 is maintained by body supports formed as surface protrusions from one or more interior surfaces of external housing 16. Further, although air gap 136 has been shown and described as being present at each of first side 104, second side 106, third side 108, and fourth side 110 of vibration damper body 18, the invention contemplates an embodiment in which air gap 136 is present on fewer, or more sides of vibration damper body 18. In one embodiment of the invention, air gap 136 is maintained without any contact between vibration damper body 18 and external housing 16. In this embodiment, the lower surface 131 of vibration damper body 18 may be secured to floor 133 of external housing so that no additional stabilization of vibration damper body 18 by external housing 18 is required.

As shown in FIG. 1, the flow of gas produced by the flow generator is provided to the patient via a patient circuit 156, which is a flexible hose, having one end coupled to an outlet 157 on external housing 16. A patient interface 158 is provided at the other end of the patient circuit. Patient interface 158 is any device adapted to coupled the patient circuit to the airway of a patient including a nasal mask, nasal/oral mask, nasal cannula, tracheal tube, endo-tracheal tube, hood, full face mask, etc.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas delivery system comprising:
   an external housing;
   a flow generator disposed in the external housing, wherein the flow generator includes a flow generator housing having a peripheral surface;
   a vibration damper body disposed within the external housing and formed of one or more compliant materials shaped to be complementary to the peripheral surface of the flow generator housing so as to engage the peripheral surface of the flow generator housing, and wherein the vibration damper body and flow generator housing are configured to form, when engaged, an air gap between a lower housing portion of the flow generator housing and the vibration damper body.

2. The system of claim 1, further comprising at least one support structure disposed on the peripheral surface of the flow generator housing, and wherein the vibration damper body forms at least one support surface adapted to be complementary to, and engage with, the at least one support structure associated with the flow generator housing.

3. The system of claim 2, wherein the at least one support surface is formed as at least one recess in the vibration damper body.

4. The system of claim 1, wherein the vibration damper body is produced from a single piece of compliant material.

5. The system of claim 1, wherein the vibration damper body is formed from a plurality of components produced from the one or more compliant materials, the plurality of components being fitted, adhered, or otherwise bonded to one another.

6. The system of claim 1, wherein spaced regions on a peripheral surface of the vibration damper body are in contact with the external housing while forming an air gap therebetween.

7. The system of claim 6, wherein the spaced regions comprise at least one protruding rib.

8. The system of claim 1, further comprising a cover assembly that is positioned over the flow generator housing to secure the engagement between the flow generator housing and the vibration damper body.

9. The system of claim 8, wherein the cover assembly comprises a vibration damping material that contacts the flow generator housing.

10. The system of claim 8, wherein the vibration damper body includes a cavity therein, and wherein the cover assembly is positioned over an opening of the cavity by fastening the cover assembly to the external housing.

11. The system of claim 1, wherein the vibration damper body includes a lower surface mounted on a bottom surface of the external housing and a peripheral surface formed such that an air gap is formed between the peripheral surface of the vibration damper body and the external housing.

12. A gas delivery system comprising:
   an external housing;
   a flow generator disposed in the external housing, the flow generator having a flow generator housing forming a flow outlet;
   a vibration damper body disposed within the external housing and formed of one or more compliant materials shaped to provide an upper surface having a portion thereof that is complementary to a peripheral surface of the flow generator housing so as to engage the peripheral surface of the flow generator housing, the upper surface providing a flow outlet seating portion that seats the flow outlet on top of the vibration damper body, wherein the vibration damper body is configured such that when engaged with the flow generator housing at least one air gap is formed between a lower housing portion of the flow generator housing and the vibration damper body.

13. The system of claim 12, wherein the vibration damper body includes a lower surface mounted on a bottom surface of the external housing and a peripheral surface formed such that at least one air gap is formed between the peripheral surface of the vibration damper body and the external housing.

14. The system of claim 12, wherein the at least one air gap is formed between a portion of the upper surface of the vibration damper body and the lower housing portion of the flow generator housing when the upper surface of the vibration damper body engages the peripheral surface of the flow housing generator.

15. The system of claim 12, wherein a flow of gas is directed from the flow outlet to an outlet formed in the external housing.

16. The system of claim 12, further comprising a cover assembly that is positioned over the flow generator housing, the flow outlet extending from the flow generator housing such that the flow outlet protrudes out from under the cover assembly.

17. A gas delivery system comprising:
   an external housing;
   a flow generator means including a flow generator means housing;
   a vibration damper means formed of one or more compliant materials shaped to be complementary to and engage with a peripheral surface of the flow generator means housing,
   wherein the flow generator means and the vibration damper means are disposed in the external housing, and wherein an air gap is formed between a lower portion of the flow generator means housing and the vibration damper means when the peripheral surface of the flow generator means housing and the vibration damper means are engaged.

\* \* \* \* \*